(12) United States Patent
Tan et al.

(10) Patent No.: US 11,835,508 B2
(45) Date of Patent: Dec. 5, 2023

(54) MODEL TEST DEVICE FOR GROUND COLLAPSE CAUSED BY PIPELINE LEAKAGE

(71) Applicant: China University Of Geosciences, Wuhan (CN)

(72) Inventors: Fei Tan, Wuhan (CN); Zhongmin Mao, Wuhan (CN); Yuyong Jiao, Wuhan (CN); Lingling He, Wuhan (CN); Jiahe Lv, Wuhan (CN); Junpeng Zou, Wuhan (CN); Yi Cheng, Wuhan (CN); Fubin Tu, Wuhan (CN)

(73) Assignee: CHINA UNIVERSITY OF GEOSCIENCES, Wuhan (CN)

( * ) Notice: Subject to any disclaimer, the term of this patent is extended or adjusted under 35 U.S.C. 154(b) by 443 days.

(21) Appl. No.: 17/235,685

(22) Filed: Apr. 20, 2021

(65) Prior Publication Data
US 2022/0179122 A1    Jun. 9, 2022

(30) Foreign Application Priority Data
Dec. 3, 2020   (CN) .......................... 202011408855.X

(51) Int. Cl.
*G01N 33/24*    (2006.01)
*G01N 3/36*    (2006.01)
*G01V 99/00*    (2009.01)

(52) U.S. Cl.
CPC ............... *G01N 33/24* (2013.01); *G01N 3/36* (2013.01); *G01V 99/005* (2013.01); *G01N 2203/0067* (2013.01); *G01N 2203/0286* (2013.01); *G01N 2203/0641* (2013.01)

(58) Field of Classification Search
CPC ...................................................... G01N 33/24
See application file for complete search history.

(56) References Cited

FOREIGN PATENT DOCUMENTS

| CN | 106018736 A | * | 10/2016 | |
|---|---|---|---|---|
| CN | 105510560 B | * | 8/2017 | ............. G01N 33/24 |
| CN | 110044710 A | * | 7/2019 | |
| CN | 111337650 A | * | 6/2020 | ............. E02D 33/00 |
| CN | 217587210 U | * | 10/2022 | |
| WO | WO-2022088454 A1 | * | 5/2022 | ......... G01N 15/0826 |

* cited by examiner

*Primary Examiner* — Ryan D Walsh
(74) *Attorney, Agent, or Firm* — Rachel K. Pilloff; Sean A. Passino; Pilloff Passino & Cosenza LLP

(57) ABSTRACT

The present invention discloses a model test device for ground collapse caused by pipeline leakage, including a sand box, a pipeline water circulation device, a groundwater replenishment device, a water storage tank and a water head measuring pipe set. The sand box includes a sand box body and a mesh sieve plate. There are two mesh sieve plate which divides an inner cavity of the sand box into a penetration cavity and a test cavity. Corresponding positions on the side wall of the test cavity are provided with a tunnel construction hole and a plurality of pipe mounting hole groups, respectively. One side wall of the test cavity is provided with a plurality of rows. There is a plurality of rows of water head measuring hole groups, and each row is provided with a plurality of the water head measuring hole groups.

10 Claims, 4 Drawing Sheets

MODEL TEST DEVICE FOR GROUND COLLAPSE CAUSED BY PIPELINE LEAKAGE

FIELD OF THE INVENTION

The present invention relates to the field of test simulation technology of ground collapse, and particularly to a model test device for ground collapse caused by pipeline leakage.

BACKGROUND OF THE INVENTION

During the use of urban municipal pipelines, with the increase in the number of years of use, probabilities of damage and leakage of the pipeline increase due to factors such as water corrosion in the pipeline and groundwater corrosion, ground loads, pipeline operating loads, temperature stresses, and underground space engineering construction disturbances. The damaged pipeline provides a seepage channel for groundwater. When the pressure difference between the inside and outer side of the pipeline reaches a certain condition, a seepage destructive force acting on pipeline-covering soil exceeds an anti-seepage destructive force between the soil particles, and a covering soil structure is destroyed. Therefore, soil-body particles flow into the pipeline with groundwater, thereby causing water and soil loss. With the loss of the soil covered by the pipeline, a cavity is formed above the pipeline and continues to expand to the ground, eventually resulting in a ground collapse under an action of ground loads. The ground collapse generally has the features of concealment, suddenness, mass occurrence and serious damage, which are likely to cause relatively large casualties and economic losses. The present invention is of great significance for revealing a disaster mechanism of the ground collapse caused by pipeline leakage, formulating effective ground collapse prevention measures, and preventing occurrence of the ground collapse.

An indoor physical model test is currently a main research method for the research on the disaster mechanism of this type of ground collapse. Test data obtained through monitoring can directly reflect occurrence of a disaster. However, this type of the current physical model test device has the following shortcomings: ① a supply source of groundwater at a leakage point of the pipeline is ignored, especially when the ground is a road pavement with a good water-proof effect. a main source of the groundwater at the leakage point of the pipeline is lateral replenishment of a water-bearing stratum; ② it is impossible to quantitatively study influence of buried depth of groundwater head on a catastrophic process of ground collapse caused by pipeline leakage; ③ it is impossible to quantitatively study a coupling effect produced by damage of a plurality of pipeline in the same area on the catastrophic process of the ground collapse caused by the pipeline leakage; ④ it is impossible to qualitatively study influence of tunnel construction around the pipeline on the catastrophic process of the ground collapse caused by the pipeline leakage. This patent invents a model test device for ground collapse caused by pipeline leakage, which is used to study depths of different groundwater heads, and can consider the coupling effect of simultaneous leakage of a plurality of the pipelines, and the disaster mechanism of the ground collapse caused by the pipeline leakage under a multi-factor influence of the pipeline near the tunnel construction.

SUMMARY OF THE INVENTION

The objective of the present invention is to provide a model test device for ground collapse caused by pipeline leakage to solve the forgoing problems in the prior art, and to realize the simulation of lateral replenishment of a water-bearing stratum located at an underground soil layer of a high water-impermeability road surface. The model test device can quantitatively study influence of buried depth of groundwater head on a catastrophic process of ground collapse caused by pipeline leakage. The model test device can quantitatively study a coupling effect produced by damage of a plurality of pipeline in the same area on the catastrophic process of the ground collapse caused by the pipeline leakage. The model test device can qualitatively study influence of tunnel construction around the pipeline on the catastrophic process of the ground collapse caused by the pipeline leakage.

In order to achieve the forgoing objectives, the present invention provides the following solutions:

The present invention provides a model test device for ground collapse caused by pipeline leakage, including a sand box, a pipeline water circulation device, a groundwater replenishment device, a water storage tank, and a water head measuring pipe group.

The sand box includes a sand box body and a mesh sieve plate. The sand box body is a cubic uncapped structure. There are two mesh sieve plates which are both parallel to the same side of the sand box body. The mesh sieve plate is fixedly connected to the inner wall of the sand box body and divides an inner cavity of the sand box body into three cavities, which are two identical penetration cavities and one test cavities, respectively. The penetration cavity is arranged on both sides of the test cavity.

The two opposite side walls of the test cavity are provided with a tunnel construction hole and a plurality of pipeline mounting hole groups, respectively. The pipeline mounting hole groups are communicated to the pipeline water circulation device.

One of the side walls of the test cavity is provided with a plurality of rows of water head measuring hole groups and each row is provided with a plurality of the water head measuring hole groups. The water head measuring hole groups are communicated to the water head measuring pipe groups.

The side wall of the penetration cavity is opened and provided with a water injecting port. The groundwater replenishment device is communicated to the penetration cavity through the water injecting port. Components connected by the two penetration cavities are completely correspondingly arranged.

The water storage tank is a cubic uncapped structure. There are two groups of the groundwater replenishment devices which are communicated to the water storage tank, respectively. The bottom of the side of the water storage tank is opened and provided with a water inlet hole. The groundwater replenishment device is communicated to the water storage tank through the water inlet hole.

Preferably, the sand box body is divided into three cavities by the mesh sieve plate. the penetration cavity completes water replenishment to the test cavity, respectively, which can fully simulate an infiltration state of water and soil in a natural environment, especially simulating more realistically an actual situation of fluctuation and change of the groundwater head after the soil covered by the pipeline is laterally replenished by the groundwater when a simulation ground is a municipal road, thereby laying a foundation for completion of subsequent tests.

Preferably, when blockage of the pipe mounting hole that is compatible with the pipe mounting hole group is flexibly adjusted, a suitable pipe mounting hole group can be selected for testing, and finally, blockage of a tunnel construction hole that is compatible with the tunnel construction hole can be opened according to needs to study influence of tunnel construction around the pipeline on the catastrophic process of the ground collapse caused by the pipeline leakage.

Preferably, the pipe mounting hole group is arranged in a plum blossom shape, which can realize research on influence of a coupling effect produced by damage of a plurality of horizontal or vertical proximity pipelines in the same area on the catastrophic process of the ground collapse caused by the pipeline leakage.

Preferably, both sides of the sand box body are opened and provided with the water injecting port and communicated to the groundwater replenishment device, which realizes replenishment of water to the test cavity through the groundwater replenishment device, and simulates a situation that soil covered by the pipeline is laterally replenished by the groundwater.

There are two groups of the groundwater replenishment devices. The groundwater replenishment device includes a high-level water tank, an overflow pipe, a water outlet pipe, a water injecting pipe, a water injecting pump, a water valve, and an adjustable bracket. The high-level water tank is a cubic structure. The top surface of the high-level water tank is fixedly connected to the adjustable bracket. The bottom surface of the high-level water tank is opened and provided with a water injecting hole and a water outlet hole. The top of one side of the high-level water tank is provided with an overflow hole. One end of the water injecting pipe is communicated to the high-level water tank through the water injecting hole, and the other end thereof is communicated to the water storage tank through the water inlet hole. The water valve and the water injecting pump are both arranged on the water injecting pipe. One end of the water outlet pipe is communicated to the high-level water tank through the water outlet hole, and the other end thereof is communicated to the penetration cavity through the water injecting port. One end of the overflow pipe is communicated to the high-level water tank through the overflow hole, and the other end thereof extends to the inside of the water storage tank.

Preferably, water in the water storage tank is pumped out through the water injecting pipe and the water injecting pump, sent into the high-level water tank, and then injected into the penetration cavity by gravity through the water outlet pipe. During the process, if the adjustable bracket connected to the high-level water tank is adjusted, a water head output by the high-level water tank can be adjusted.

The adjustable bracket includes a telescopic rod, a base, and a fixing beam. One end of the telescopic rod is vertically fixedly connected to the top surface of the base, and the other end thereof is fixedly connected to one end of the fixing beam. The other end of the fixing beam is fixedly connected to the top surface of the high-level water tank.

Preferably, the adjustable bracket realizes adjustment of the water head of the high-level water tank fixed on the fixing beam by adjusting a height of the telescopic bracket.

The pipeline water circulation device includes a filter water tank, a booster pump, a water inlet pipeline group, a leakage pipeline, and a water return pipeline group.

The filter water tank is a cubic uncapped structure. The filter water tank includes a filter box body, a coarse sieve partition plate, and a fine sieve partition plate. The coarse sieve partition plate and the fine sieve partition plate are vertically and fixedly connected to the inner wall of the filter box body, respectively, and divide the filter box body into three cavities, respectively, which are a clean water cavity, a fine sand sedimentation cavity and a coarse sand sedimentation cavity. The clean water cavity and the coarse sand sedimentation cavity are arranged on both sides of the fine sand sedimentation cavity. The middle and top of the fine sieve partition plate are both provided with a plurality of water passing holes. The top of the coarse sieve partition plate is provided with the plurality of water passing holes;

The water inlet pipeline group includes a main water inlet pipe, a sub water inlet pipe, a sub-control water inlet valve, and a pressure gauge. One end of the main water inlet pipe passes through one side wall of the clean water cavity and is communicated to the clean water cavity, and the other end thereof is communicated to one end of the sub water inlet pipe. The booster pump is arranged at the main water inlet pipe. The other end of the sub water inlet pipe is communicated to the leakage pipeline. There is a plurality of the sub water inlet pipes. The sub-control water inlet valve and the pressure gauge are both arranged on the sub water inlet pipe. A water inlet port of the pressure gauge is communicated to a water outlet port of the sub-control water inlet valve. There are a plurality of the sub-control water inlet valves and a plurality of the pressure gauges, respectively.

The water return pipeline group includes a main water return pipe, a sub water return pipe, a sub-control water return valve, a water and soil measuring valve, and a three-link. One end of a main water return pipe passes through the side wall of the coarse sand sedimentation cavity and is communicated to the coarse sand sedimentation cavity, and the other end thereof is communicated to one end of the sub water return pipe. The other end of the sub water return pipe is communicated to the leakage pipeline. There is a plurality of the sub water return pipes. The sub-control water return valve and the three-link are both arranged on the sub water return pipe. A water inlet port of the sub-control water return valve is communicated to a water outlet port of the three-link. There are a plurality of the sub-control water return valves and a plurality of the three-links, respectively. A remaining port of the three-link is fixedly connected to the water and soil measuring valve. There is a plurality of the water and soil measuring valves.

Preferably, there are a plurality of the sub water return pipelines and a plurality of the sub water inlet pipelines, which can provide the corresponding selections for different test scenarios.

Preferably, the sub water return pipeline and the sub water inlet pipeline are both provided with valves. The water inlet port of the pressure gauge is communicated to the water outlet port of the sub-control water inlet valve, so as to realize quantitative control of a water flow head in the pipeline.

Preferably, the three-link and the water and soil measuring valve arranged on the sub water return pipeline can detect water flowing back from the sub water return pipeline according to the needs of the test.

There is a plurality of groups of the leakage pipelines. The leakage pipeline includes an outer sleeve pipe and an embedded diameter-changing pipe. There are a plurality of the outer sleeve pipes and a plurality of the embedded diameter-changing pipes. Ends of a plurality of the outer sleeve pipes are communicated to the pipeline mounting hole group corresponding to a position and sleeved on the outer side of a small diameter of the embedded diameter-changing pipe, and the other ends thereof are communicated to the other ends of the sub water inlet pipe through the pipeline mounting hole group corresponding to the position. One end of a large diameter of the embedded diameter-changing pipe is communicated to the sub water return pipe, and the middle of the outer sleeve pipe is opened and provided with a leakage seam.

Preferably, the outer sleeve pipe is sleeved on the outer side of the small diameter of the embedded diameter-changing pipe. The leakage seam is opened and provided in the middle of the outer sleeve pipe. Through expansion and contraction of the embedded diameter-changing pipe, the leakage seam can be opened and closed to achieve different objectives of the test.

The end of the small diameter of the outer sleeve pipe has a length equal to that of the embedded diameter-changing pipe.

Preferably, the end of the small diameter of the outer sleeve pipe has a length equal to that of the embedded diameter-changing pipe, which ensures that the leakage seam can be opened and closed through plugging and unplugging operations of the embedded diameter-changing pipe.

The water head measuring pipe group includes a measuring pipe, a fixing plate, and a connecting pipe.

The number of the measuring pipes is not less than that of the water head measuring hole groups. The measuring pipes are vertically and fixedly connected to one side of the fixing plate. One end of the measuring pipes is opened, and the other end thereof is communicated to one end of the connecting pipe. The other end of the connecting pipe is communicated to the test cavity through the water head measuring hole group.

Preferably, the water head measuring hole group is communicated to the measuring pipe group to realize measurement of a water head in the test cavity.

The outer side of the measuring pipe is provided with a scale. The measuring pipe is a transparent glass pipe or a transparent plastic pipe.

A volume ratio of the test cavity to the penetration cavity is 3-10.

The mesh sieve plate has a specification of 100 meshes to 500 meshes.

Preferably, the mesh sieve plate is provided with specific specifications, so that water infiltration in the penetration cavity is realized during use, and the loss of sand is avoided.

The present invention discloses the following technical effects:

(1) Simple structure, convenient processing and assembly, low costs, safety and reliability.

(2) Equipment is simple to operate and is suitable for a physical model test of ground collapse caused by pipeline leakage.

(3) The present invention can realize simulation of lateral replenishment of water from soil covered by a pipeline. In addition, the present invention can also realize adjustment and real-time monitoring of groundwater head of model soil, which can simulate more realistically, especially simulating more realistically an actual situation of fluctuation and change of the groundwater head after the soil covered by the pipeline is laterally replenished by the groundwater when a simulation ground is a municipal road.

(4) Through the pipeline mounting hole group, the present invention can realize physical simulation study of a disaster mechanism of ground collapse when a plurality of the pipelines have leakage at the same time. At the same time, by adjusting a valve and a water pump of the present invention, water volume and water pressure of the corresponding pipeline can be flexibly adjusted, which plays a great role in adjusting test parameters to achieve a comprehensive simulation of realistic conditions.

(5) Through a tunnel construction hole, physical simulation study of an action mechanism of tunnel construction in a process of ground collapse caused by pipeline leakage can be realized.

(6) The entire model device can realize self-circulation of test water and collection of lost soil, which reduces workload of testers in a test process while saving water.

BRIEF DESCRIPTION OF THE FIGURES

In order to explain embodiments of the present invention or the technical solutions in the prior art more clearly, the following briefly introduces the drawings that need to be used in the embodiments. Obviously, the drawings in the following description are only some of embodiments of the present invention. The person skilled in the art can obtain other drawings based on these drawings without creative work.

Figure 1:
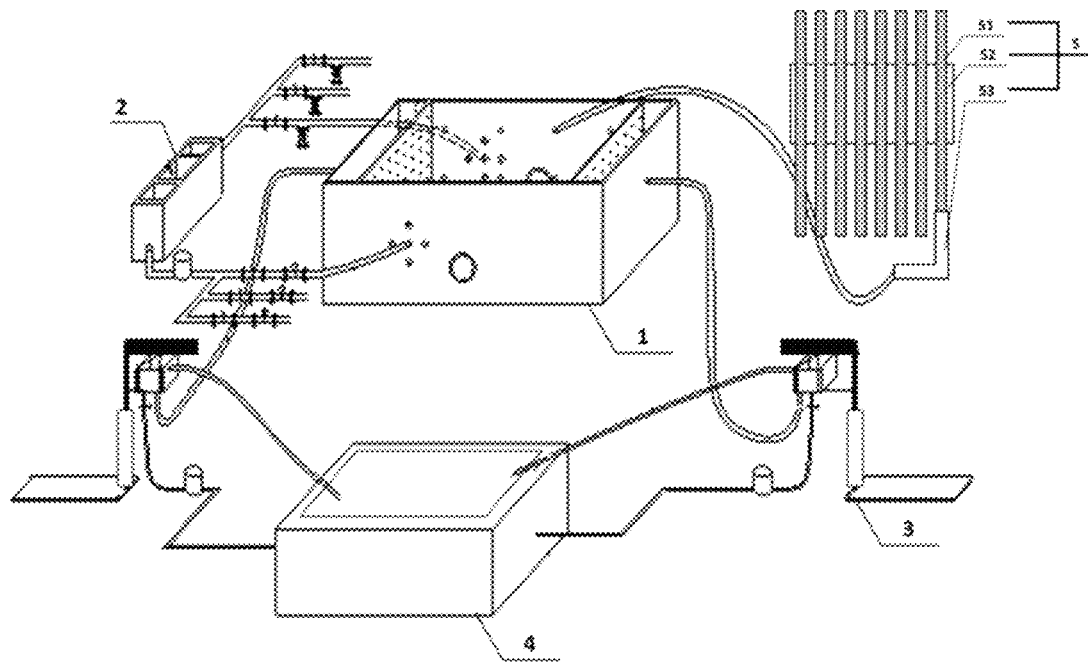
FIG. 1 is a schematic structural diagram of the present invention.
Figure 2:
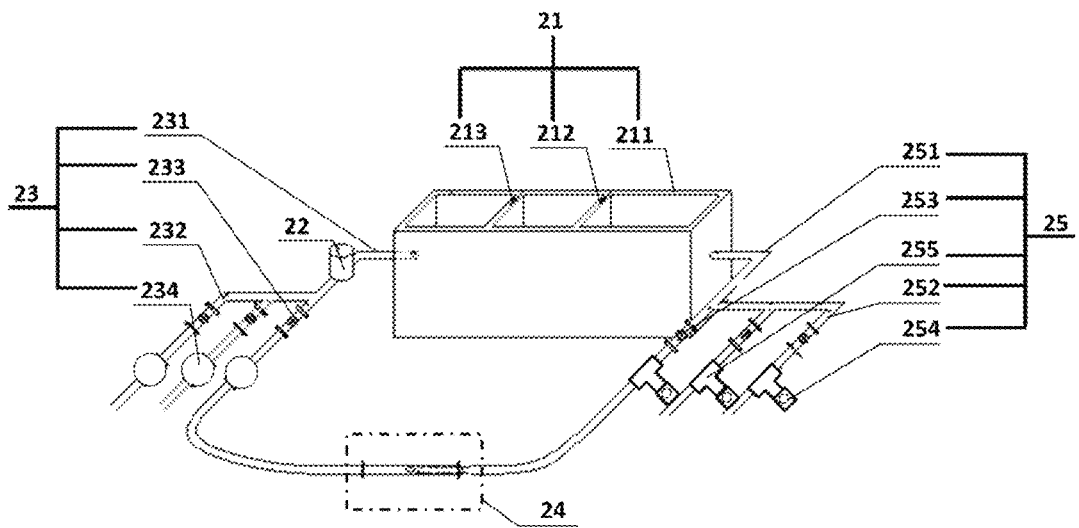
FIG. 2 is a schematic diagram of a pipeline water circulation device.
Figure 3:
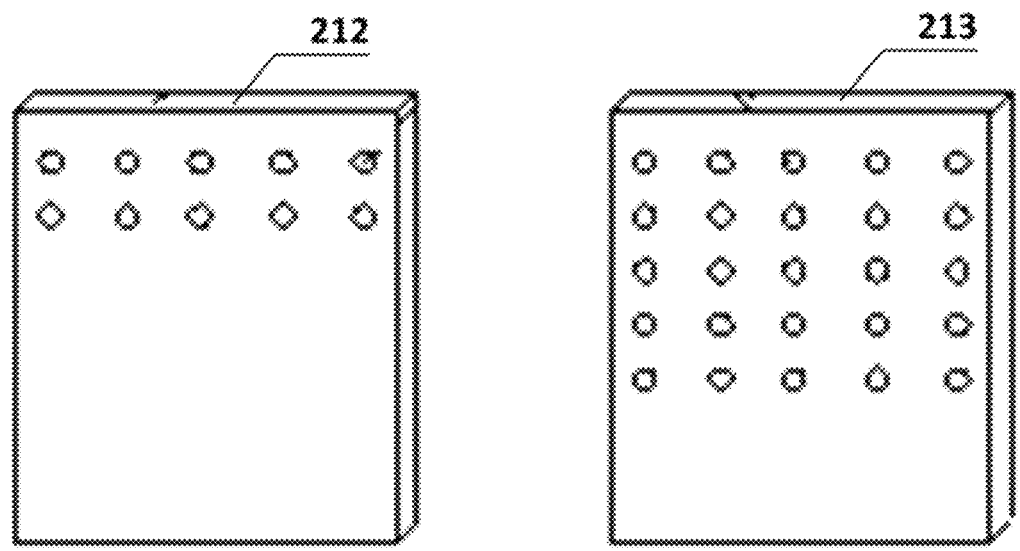
FIG. 3 is a schematic diagram of a coarse sand partition plate and a fine sand partition plate.
Figure 4:
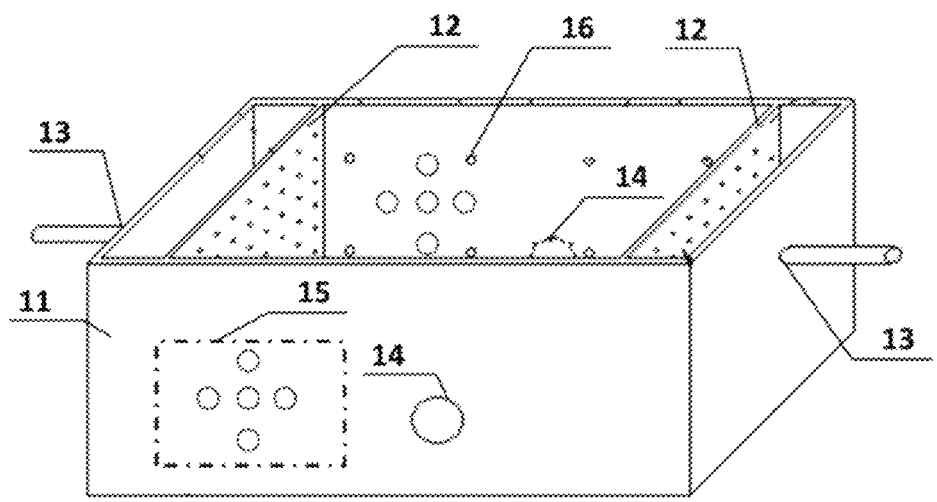
FIG. 4 is a schematic diagram of a sand box.
Figure 5:
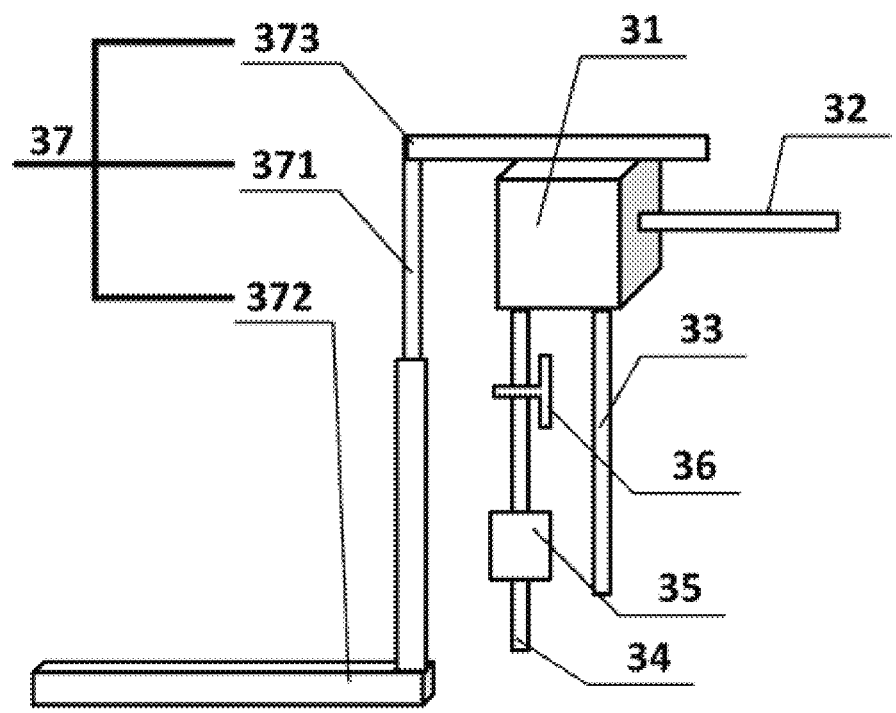
FIG. 5 is a schematic diagram of a groundwater replenishment device.
Figure 6:
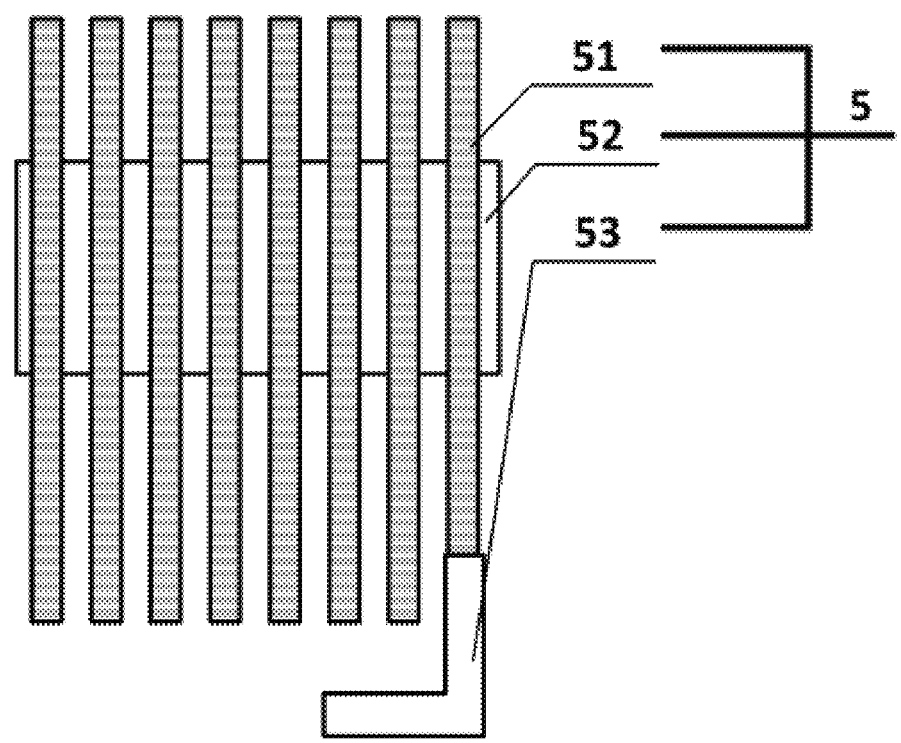
FIG. 6 is a schematic diagram of a water head measuring pipe group.
Figure 7:
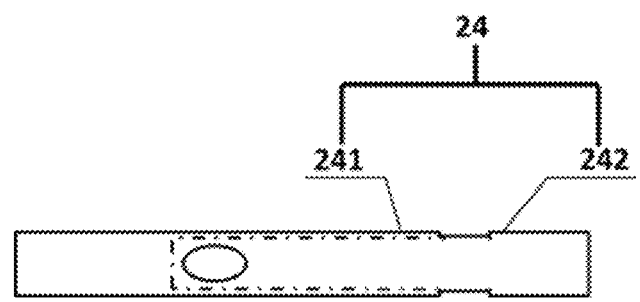
FIG. 7 is a schematic diagram of a leakage pipeline.

Sand Box—1, Sand Box Body—11, Mesh Sieve Plate—12, Water Injecting Port—13, Tunnel Construction Hole—14, Pipeline Mounting Hole Group—15, Water Head Measuring Hole Group—16, Pipeline Water Circulation Device—2, Filter Water Tank—21, Filter Box—211, Coarse Sand Partition Plate—212, Fine Sand Partition Plate—213, Booster Pump—22, Water Inlet Pipeline Group—23, Main Water Inlet Pipeline—231, Sub Water Inlet Pipeline—232, Sub-Control Water Inlet Valve—233, Pressure Gauge—234, Leakage Pipeline—24, Outer Sleeve Pipe—241, Embedded Diameter—Changing Pipe—242, Water Return Pipeline Group—25, Main Water Return Pipe—251, Sub Water Return Pipe—252, Sub—Control Water Return Valve—253, Water And Soil Measuring Valve—254, Three-Link—255, Groundwater Replenishment Device—3, High-Level Water Tank—31, Overflow Pipe—32, Water Outlet Pipe —33, Water Injecting Pipe —34, Water Injecting Pump—35, Water Valve—36, Adjustable Bracket—37, Telescopic Rod—371, Base—372, Fixing Beam—373, Water Storage Tank—4, Water Head Measuring Pipe Group—5, Measuring Pipe—51, Fixing Plate—52, Connecting Pipe—53.

DESCRIPTION OF THE INVENTION

The following clearly and completely describes the technical solutions in embodiments of the present invention in conjunction with the drawings in the embodiments of the present invention. Obviously, the described embodiments are only a part of the embodiments of the present invention, rather than all embodiments. Based on the embodiments of the present invention, all other embodiments obtained by the person skilled in the art without creative work shall fall within the protection scope of the present invention.

In order to make the forgoing objectives, features and advantages of the present invention more obvious and easy to understand, the present invention is further described in detail with reference to the drawings and specific embodiments.

The present invention provides a model test device for ground collapse caused by pipeline leakage, including a sand box 1, a pipeline water circulation device 2, a groundwater replenishment device 3, a water storage tank 4 and a water head measuring pipe group 5.

The sand box 1 comprises a sand box body 11 and a mesh sieve plate 12. The sand box body 11 is a cubic uncapped structure. There are two mesh sieve plates 12 which are both parallel to the same side of the sand box body 11. The mesh sieve plate 12 is fixedly connected to the inner wall of the sand box body 11 and divides an inner cavity of the sand box body 11 into three cavities, which are two identical penetration cavities and one test cavities, respectively. The penetration cavity is arranged on both sides of the test cavity.

The two opposite side walls of the test cavity are provided with a tunnel construction hole 14 and a plurality of pipeline mounting hole groups 15, respectively. The pipeline mounting hole groups 15 are communicated to the pipeline water circulation device 2.

One of the side walls of the test cavity is provided with a plurality of rows of water head measuring hole groups 16. Each row is provided with a plurality of the water head measuring hole groups 16. The water head measuring hole groups 16 are communicated to the water head measuring pipe groups 5.

The side wall of the penetration cavity is opened and provided with a water injecting port 13. The groundwater replenishment device 3 is communicated to the penetration cavity through the water injecting port 13. Components connected by the two penetration cavities are completely correspondingly arranged.

The water storage tank 4 is a cubic uncapped structure. There are two groups of the groundwater replenishment devices 3 which are communicated to the water storage tank 4, respectively. The bottom of the side of the water storage tank 4 is opened and provided with a water inlet hole. The groundwater replenishment device 3 is communicated to the water storage tank 4 through the water inlet hole.

There are two groups of the groundwater replenishment devices 3. The groundwater replenishment device 3 includes a high-level water tank 31, an overflow pipe 32, a water outlet pipe 33, a water injecting pipe 34, a water injecting pump 35, a water valve 36, and an adjustable bracket 37. The high-level water tank 31 is a cubic structure. The top surface of the high-level water tank 31 is fixedly connected to the adjustable bracket 37. The bottom surface of the high-level water tank 31 is opened and provided with a water injecting hole and a water outlet hole. The top of one side of the high-level water tank 31 is provided with an overflow hole. One end of the water injecting pipe 34 is communicated to the high-level water tank 31 through the water injecting hole, and the other end thereof is communicated to the water storage tank 4 through the water inlet hole. The water valve 36 and the water injecting pump 35 are both arranged on the water injecting pipe 34. One end of the water outlet pipe 33 is communicated to the high-level water tank 31 through the water outlet hole, and the other end thereof is communicated to the penetration cavity through the water injecting port 13. One end of the overflow pipe 32 is communicated to the high-level water tank through the overflow hole 31, and the other end thereof extends to the inside of the water storage tank 4.

The adjustable bracket 37 includes a telescopic rod 371, a base 372, and a fixing beam 373. One end of the telescopic rod 371 is vertically fixedly connected to the top surface of the base 372, and the other end thereof is fixedly connected to one end of the fixing beam 373. The other end of the fixing beam 373 is fixedly connected to the top surface of the high-level water tank 31.

The pipeline water circulation device 2 includes a filter water tank 21, a booster pump 22, a water inlet pipeline group 23, a leakage pipeline 24, and a water return pipeline group 25.

The filter water tank 21 is a cubic uncapped structure. The filter water tank 21 includes a filter box body 211, a coarse sieve partition plate 212, and a fine sieve partition plate 213. The coarse sieve partition plate 212 and the fine sieve partition plate 213 are vertically and fixedly connected to the inner wall of the filter box body 211, respectively, and divide the filter box body 211 into three cavities, respectively, which are a clean water cavity, a fine sand sedimentation cavity and a coarse sand sedimentation cavity. The clean water cavity and the coarse sand sedimentation cavity are arranged on both sides of the fine sand sedimentation cavity. The middle and top of the fine sieve partition plate 213 are both provided with a plurality of water passing holes. The top of the coarse sieve partition plate 212 is provided with the plurality of water passing holes.

The water inlet pipeline group 23 includes a main water inlet pipe 231, a sub water inlet pipe 232, a sub-control water inlet valve 233, and a pressure gauge 234. One end of the main water inlet pipe 231 passes through one side wall of the clean water cavity and is communicated to the clean water cavity, and the other end thereof is communicated to one end of the sub water inlet pipe 232. The booster pump 22 is arranged at the main water inlet pipe 231. The other end of the sub water inlet pipe 232 is communicated to the leakage pipeline 24. There is a plurality of the sub water inlet pipes 232. The sub-control water inlet valve 233 and the pressure gauge 234 are both arranged on the sub water inlet pipe 232. A water inlet port of the pressure gauge 234 is communicated to a water outlet port of the sub-control water inlet valve 233. There are a plurality of the sub-control water inlet valves 233 and a plurality of the pressure gauges 234, respectively.

The water return pipeline group 25 includes a main water return pipe 251, a sub water return pipe 252, a sub-control water return valve 253, a water and soil measuring valve 254, and a three-link 255. One end of a main water return pipe 251 passes through the side wall of the coarse sand sedimentation cavity and is communicated to the coarse sand sedimentation cavity, and the other end thereof is communicated to one end of the sub water return pipe 252. The other end of the sub water return pipe 252 is communicated to the leakage pipeline 24. There is a plurality of the sub water return pipes 252. The sub-control water return valve 253 and the three-link 255 are both arranged on the sub water return pipe 252. A water inlet port of the sub-control water return valve 253 is communicated to a water outlet port of the three-link 255. There are a plurality of the sub-control water return valves 253 and a plurality of the three-links 255, respectively. A remaining port of the three-link 255 is fixedly connected to the water and soil measuring valve 254. There is a plurality of the water and soil measuring valves 254.

There is a plurality of groups of the leakage pipelines 24, and the leakage pipeline 24 includes an outer sleeve pipe 241 and an embedded diameter-changing pipe 242. There are a plurality of the outer sleeve pipes 241 and a plurality of the embedded diameter-changing pipes 242. Ends of a plurality of the outer sleeve pipes 241 are communicated to the pipeline mounting hole group 15 corresponding to a position and sleeved on the outer side of a small diameter of the embedded diameter-changing pipe 242, and the other ends thereof are communicated to the other ends of the sub water inlet pipe 232 through the pipeline mounting hole group 15 corresponding to the position. One end of a large diameter of the embedded diameter-changing pipe 242 is communicated to the sub water return pipe 252, and the middle of the outer sleeve pipe 241 is opened and provided with a leakage seam.

The end of the small diameter of the outer sleeve pipe 241 has a length equal to that of the embedded diameter-changing pipe 242.

The water head measuring pipe group 5 includes a measuring pipe 51, a fixing plate 52, and a connecting pipe 53.

The number of the measuring pipes 51 is not less than that of the water head measuring hole groups 16. The measuring pipes 51 are vertically and fixedly connected to one side of the fixing plate 52. One end of the measuring pipes 51 is opened, and the other end thereof is communicated to one end of the connecting pipe 53. The other end of the connecting pipe 53 is communicated to the test cavity through the water head measuring hole group 16.

The outer side of the measuring pipe 51 is provided with a scale. The measuring pipe 51 is a transparent glass pipe or a transparent plastic pipe.

A volume ratio of the test cavity to the penetration cavity is 3-10.

The mesh sieve plate has a specification of 100 meshes to 500 meshes.

In an embodiment of the present invention, paving of a model and height adjustment of the high-level water tank 31 are completed in the test cavity. The sub-control water inlet valve 233 and the sub-control water return valve 253 are opened. The water valves 36 of two sets of the groundwater replenishment devices 3 are opened. The water injecting pump 35 is powered on. Replenishment of groundwater in the model soil and the adjustment of the water head are completed through two sets of the groundwater replenishment devices 3. When a water head value in the measured pipe 51 reaches an initial value of a model groundwater head in the test, the groundwater replenishment of the model soil is completed. At this time, the leakage seam can be opened by pulling the embedded diameter-changing pipe 242. A water pressure in the leakage pipeline 24 can be adjusted through the sub-control water inlet valve 233, and the pressure gauge 234 can be used to realize the real-time measurement of water pressure. By pressing in and pulling the embedded diameter-changing pipe 242, an opening level of the leakage seam is controlled. The water and soil measuring valve 254 is used to collect and measure water and soil returned in the sub water return pipe 252. The water head measuring pipe group 5 is used to realize real-time monitoring of a groundwater head at each water head monitoring point of a soil body. The sand box 11 made of a transparent material is used to realize direct observation of a process of water and soil loss in a soil body model. By opening the tunnel construction hole to perform blockage, research on impact of tunnel construction on a disaster-causing process of the ground collapse caused by the pipeline leakage can be performed.

The present invention discloses the following technical effects:

(1) Simple structure, convenient processing and assembly, low costs, safety and reliability.

(2) Equipment is simple to operate and is suitable for a physical model test of ground collapse caused by pipeline leakage.

(3) The present invention can realize simulation of lateral replenishment of water from soil covered by a pipeline. In addition, the present invention can also realize adjustment and real-time monitoring of groundwater head of model soil, which can simulate more realistically, especially simulating more realistically an actual situation of fluctuation and change of the groundwater head after the soil covered by the pipeline is laterally replenished by the groundwater when a simulation ground is a municipal road.

(4) Through the pipeline mounting hole group, the present invention can realize physical simulation study of a disaster mechanism of ground collapse when a plurality of the pipelines have leakage at the same time. At the same time, by adjusting a valve and a water pump of the present invention, water volume and water pressure of the corresponding pipeline can be flexibly adjusted, which plays a great role in adjusting test parameters to achieve a comprehensive simulation of realistic conditions.

(5) Through a tunnel construction hole, physical simulation study of an action mechanism of tunnel construction in a process of ground collapse caused by pipeline leakage can be realized.

(6) The entire model device can realize self-circulation of test water and collection of lost soil, which reduces workload of testers in a test process while saving water.

In the description of the present invention, it should be understood that the orientation or positional relationship indicated by the terms such as "longitudinal", "lateral", "upper", "lower", "front", "rear", "left", "right", "vertical", "horizontal", "top", "bottom", "inner", "outer", etc. are based on the orientation or positional relationship shown in the drawings, and are only for the convenience of describing the present invention, rather than indicating or implying that a device or element referred to should have a specific orientation, be configured and operated in a specific orientation, and therefore cannot be understood as a limitation to the present invention.

The forgoing embodiments only describe the preferred mode of the present invention, and do not limit the scope of the present invention. Without departing from the design spirit of the present invention, the person skilled in the art can make variations and improvements to the technical solutions of the present invention, which should fall within the protection scope determined by the claims of the present invention.

The invention claimed is:

1. A model test device for ground collapse caused by pipeline leakage, comprising: a sand box (1), a pipeline water circulation device (2), a groundwater replenishment device (3), a water storage tank (4) and a water head measuring pipe group (5);

the sand box (1) comprises a sand box body (11) and a mesh sieve plate (12); the sand box body (11) is a cubic uncapped structure; there are two mesh sieve plates (12) which are both parallel to the same side of the sand box body (11); the mesh sieve plate (12) is fixedly connected to the inner wall of the sand box body (11) and divides an inner cavity of the sand box body (11) into three cavities, which are two identical penetration cavities and one test cavity, respectively; the penetration cavity is arranged on both sides of the test cavity; the two opposite side walls of the test cavity are provided with a tunnel construction hole (14) and a plurality of pipeline mounting hole groups (15), respectively; the pipeline mounting hole groups (15) are communicated to the pipeline water circulation device (2);

one of the side walls of the test cavity is provided with a plurality of rows of water head measuring hole groups (16); each row is provided with a plurality of the water head measuring hole groups (16), the water head measuring hole groups (16) are communicated to the water head measuring pipe groups (5);

the side wall of the penetration cavity is opened and provided with a water injecting port (13), the groundwater replenishment device (3) is communicated to the penetration cavity through the water injecting port (13); components connected by the two penetration cavities are completely correspondingly arranged;

the water storage tank (4) is a cubic uncapped structure; there are two groups of the groundwater replenishment devices (3) which are communicated to the water storage tank (4), respectively; the bottom of the side of the water storage tank (4) is opened and provided with a water inlet hole, the groundwater replenishment device (3) is communicated to the water storage tank (4) through the water inlet hole.

2. The model test device for the ground collapse caused by the pipeline leakage according to claim 1, wherein there are two groups of the groundwater replenishment devices (3); the groundwater replenishment device (3) comprises a high-level water tank (31), an overflow pipe (32), a water outlet pipe (33), a water injecting pipe (34), a water injecting pump (35), a water valve (36), and an adjustable bracket (37); the high-level water tank (31) is a cubic structure, the top surface of the high-level water tank (31) is fixedly connected to the adjustable bracket (37); the bottom surface of the high-level water tank (31) is opened and provided with a water injecting hole and a water outlet hole, the top of one side of the high-level water tank (31) is provided with an overflow hole; one end of the water injecting pipe (34) is communicated to the high-level water tank (31) through the water injecting hole, and the other end thereof is communicated to the water storage tank (4) through the water inlet hole; the water valve (36) and the water injecting pump (35) are both arranged on the water injecting pipe (34); one end of the water outlet pipe (33) is communicated to the high-level water tank (31) through the water outlet hole, and the other end thereof is communicated to the penetration cavity through the water injecting port (13); one end of the overflow pipe (32) is communicated to the high-level water tank through the overflow hole (31), and the other end thereof extends to the inside of the water storage tank (4).

3. The model test device for the ground collapse caused by the pipeline leakage according to claim 2, wherein the adjustable bracket (37) comprises a telescopic rod (371), a base (372), and a fixing beam (373); one end of the telescopic rod (371) is vertically fixedly connected to the top surface of the base (372), and the other end thereof is fixedly connected to one end of the fixing beam (373); and the other end of the fixing beam (373) is fixedly connected to the top surface of the high-level water tank (31).

4. The model test device for the ground collapse caused by the pipeline leakage according to claim 1, wherein the pipeline water circulation device (2) comprises a filter water tank (21), a booster pump (22), a water inlet pipeline group (23), a leakage pipeline (24) and a water return pipeline group (25);

the filter water tank (21) is a cubic uncapped structure; the filter water tank (21) comprises a filter box body (211), a coarse sieve partition plate (212), and a fine sieve partition plate (213); the coarse sieve partition plate (212) and the fine sieve partition plate (213) are vertically and fixedly connected to the inner wall of the filter box body (211), respectively, and divide the filter box body (211) into three cavities, respectively, which are a clean water cavity, a fine sand sedimentation cavity and a coarse sand sedimentation cavity; the clean water cavity and the coarse sand sedimentation cavity are arranged on both sides of the fine sand sedimentation cavity; the middle and top of the fine sieve partition plate (213) are both provided with a plurality of water passing holes; the top of the coarse sieve partition plate (212) is provided with the plurality of water passing holes;

the water inlet pipeline group (23) comprises a main water inlet pipe (231), a sub water inlet pipe (232), a sub-control water inlet valve (233), and a pressure gauge (234); one end of the main water inlet pipe (231) passes through one side wall of the clean water cavity and is communicated to the clean water cavity, and the other end thereof is communicated to one end of the sub water inlet pipe (232); the booster pump (22) is arranged at the main water inlet pipe (231); the other end of the sub water inlet pipe (232) is communicated to the leakage pipeline (24); there is a plurality of the sub water inlet pipes (232); the sub-control water inlet valve (233) and the pressure gauge (234) are both arranged on the sub water inlet pipe (232), and a water inlet port of the pressure gauge (234) is communicated to a water outlet port of the sub-control water inlet valve (233), there are a plurality of the sub-control water inlet valves (233) and a plurality of the pressure gauges (234), respectively;

the water return pipeline group (25) comprises a main water return pipe (251), a sub water return pipe (252), a sub-control water return valve (253), a water and soil measuring valve (254), and a three-link (255); one end of a main water return pipe (251) passes through the side wall of the coarse sand sedimentation cavity and is communicated to the coarse sand sedimentation cavity, and the other end thereof is communicated to one end of the sub water return pipe (252); the other end of the sub water return pipe (252) is communicated to the leakage pipeline (24); there is a plurality of the sub water return pipes (252); the sub-control water return valve (253) and the three-link (255) are both arranged on the sub water return pipe (252), and a water inlet port of the sub-control water return valve (253) is communicated to a water outlet port of the three-link (255); there are a plurality of the sub-control water return valves (253) and a plurality of the three-links (255), respectively; a remaining port of the three-link (255) is fixedly connected to the water and soil measuring valve (254); there is a plurality of the water and soil measuring valves (254).

5. The model test device for the ground collapse caused by the pipeline leakage according to claim 4, wherein there is a plurality of groups of the leakage pipelines (24), and the leakage pipeline (24) comprises an outer sleeve pipe (241) and an embedded diameter-changing pipe (242); there are a plurality of the outer sleeve pipes (241) and a plurality of the embedded diameter-changing pipes (242); ends of a plurality of the outer sleeve pipes (241) are communicated to the pipeline mounting hole group (15) corresponding to a position and sleeved on the outer side of a small diameter of the embedded diameter-changing pipe (242), and the other ends thereof are communicated to the other ends of the sub water inlet pipe (232) through the pipeline mounting hole group (15) corresponding to the position; one end of a large diameter of the embedded diameter-changing pipe (242) is communicated to the sub water return pipe (252), and the middle of the outer sleeve pipe (241) is opened and provided with a leakage seam.

6. The model test device for the ground collapse caused by the pipeline leakage according to claim 5, wherein the end of the small diameter of the outer sleeve pipe (241) has a length equal to that of the embedded diameter-changing pipe (242).

7. The model test device for the ground collapse caused by the pipeline leakage according to claim 1, wherein the water head measuring pipe group (5) comprises a measuring pipe (51), a fixing plate (52), and a connecting pipe (53);

the number of the measuring pipes (51) is not less than that of the water head measuring hole groups (16); the measuring pipes (51) are vertically and fixedly connected to one side of the fixing plate (52); one end of the measuring pipes (51) is opened, and the other end thereof is communicated to one end of the connecting pipe (53); the other end of the connecting pipe (53) is communicated to the test cavity through the water head measuring hole group (16).

8. The model test device for the ground collapse caused by the pipeline leakage according to claim 7, wherein the outer side of the measuring pipe (51) is provided with a scale; the measuring pipe (51) is a transparent glass pipe or a transparent plastic pipe.

9. The model test device for the ground collapse caused by the pipeline leakage according to claim 1, wherein a volume ratio of the test cavity to the penetration cavity is 3-10.

10. The model test device for the ground collapse caused by the pipeline leakage according to claim 1, wherein the mesh sieve plate (12) has a specification of 100 mesh to 500 mesh.

* * * * *